United States Patent [19]

Röben et al.

[11] Patent Number: 4,916,120
[45] Date of Patent: Apr. 10, 1990

[54] PARASITICIDAL AVERMECTIN DERIVATIVES

[75] Inventors: Wolfgang Röben, Bergisch Gladbach; Stendel Wilhelm; Peter Andrews, both of Wuppertal, all of Fed. Rep. of Germany

[73] Assignee: Bayer Aktiengesellschaft, Leverkusen, Fed. Rep. of Germany

[21] Appl. No.: 230,221

[22] Filed: Aug. 1, 1988

[30] Foreign Application Priority Data

Aug. 19, 1987 [DE] Fed. Rep. of Germany ....... 3727648

[51] Int. Cl.$^4$ ...................... A61K 31/70; C07H 17/04
[52] U.S. Cl. ..................................... 514/30; 536/7.1; 549/264
[58] Field of Search ................ 536/7.1; 514/30; 549/264

[56] References Cited

U.S. PATENT DOCUMENTS

| | | | |
|---|---|---|---|
| 4,333,925 | 6/1982 | Buhs et al. | 536/7.1 |
| 4,349,666 | 9/1982 | Umezama et al. | 536/13.7 |
| 4,423,209 | 12/1983 | Mrozik | 536/7.1 |

Primary Examiner—Johnnie R. Brown
Assistant Examiner—Elli Peselev
Attorney, Agent, or Firm—Sprung Horn Kramer & Woods

[57] ABSTRACT

Parasiticidally active avermectin derivatives of the formula

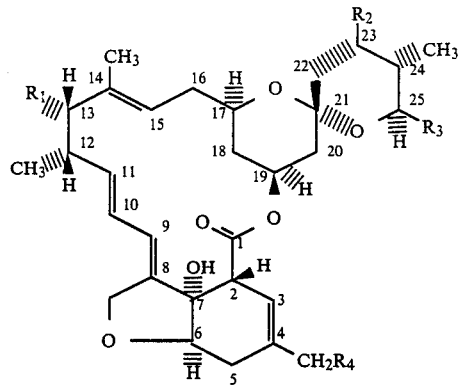

in which $R^1$ stands for hydrogen, OH, $C_{1-5}$-alkanoyloxy, α-L-oleandrosyloxy, α-L-oleandrosyl-α-L-oleandrosyloxy, 4'-$C_{1-5}$-alkanoyl-α-oleandrosyloxy or 4''-$C_{1-5}$-alkanoyl-α-L-oleandrosyl-α-L-oleandrosyloxy, $R^2$ stands for hydrogen, OH, $C_{1-5}$-alkanoyloxy, or $R^2$ stands for hydrogen when there is a double bond between C22 and C23, $R^3$ stands for straight-chain or branched alkyl or alkenyl, and $R^4$ stands for hydrogen, OH, $C_{1-5}$-alkanoyloxy, heterocyclylcarbonyloxy, or the bond between the C atoms C22 and C23 is a single or a double bond and the double bond of the cyclohexene ring can be between the C atoms C3 and C4 or between the C atoms C4 and C5.

7 Claims, No Drawings

PARASITICIDAL AVERMECTIN DERIVATIVES

The present invention relates to new avermectin derivatives, a process for their preparation, intermediates for carrying out this process and their use as parasiticides.

Avermectins are ecto- and endoparasiticides having a broad range of action. A derivative having the generic name ivermectin is on the market as a parasiticide for animals. Its action against ticks is not completely satisfactory, however.

1. The new compounds of the formula I

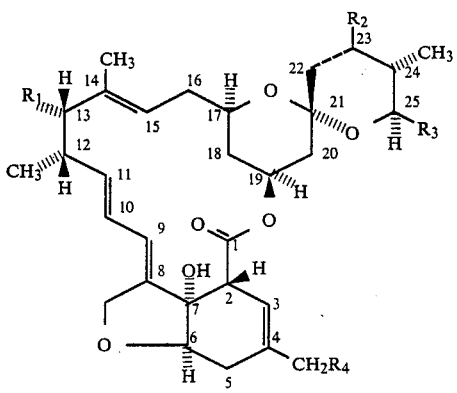

in which
  $R^1$ stands for hydrogen, OH, $C_{1-5}$-alkanoyloxy, α-L-oleandrosyloxy, α-L-oleandrosyl-α-L-oleandrosyloxy, 4'-$C_{1-5}$-alkanoyl-α-L-oleandrosyloxy or 4"-$C_{1-5}$-alkanoyl-α-L-oleandrosyl-α-L-oleandrosyloxy,
  $R^2$ stands for hydrogen, OH, $C_{1-5}$-alkanoyloxy, or $R^2$ stands for hydrogen when there is a double bond between C22 and C23,
  $R^3$ stands for straight-chain or branched alkyl or alkenyl,
  $R^4$ stands for hydrogen, OH, $C_{1-5}$-alkanoyloxy, heterocyclylcarbonyloxy, or the bond between the C atoms C22 and C23 is a single or a double bond and the double bond of the cyclohexene ring can be between the C atoms C3 and C4 or between the C atoms C4 and C5,
have now been found.

2 A process has been found for the preparation of the compounds of the formula I

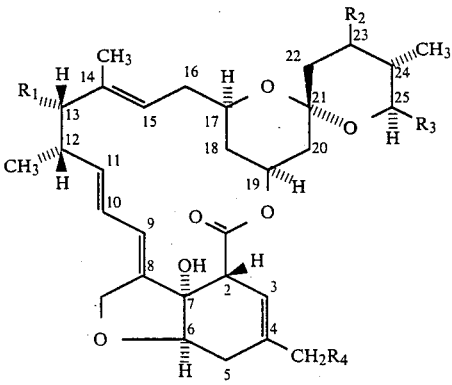

in which
  $R^1$ stands for hydrogen, OH, $C_{1-5}$-alkanoyloxy, α-L-oleandrosyloxy, α-L-oleandrosyl-α-L-oleandrosyloxy, 4'-$C_{1-5}$-alkanoyl-α-oleandrosyloxy or 4"-$C_{1-5}$-alkanoyl-α-L-oleandrosyl-α-L-oleandrosyloxy,
  $R^2$ stands for hydrogen, OH, $C_{1-5}$-alkanoyloxy, or $R^2$ stands for hydrogen when there is a double bond between C22 and C23,
which is characterized in that compounds of the formula II

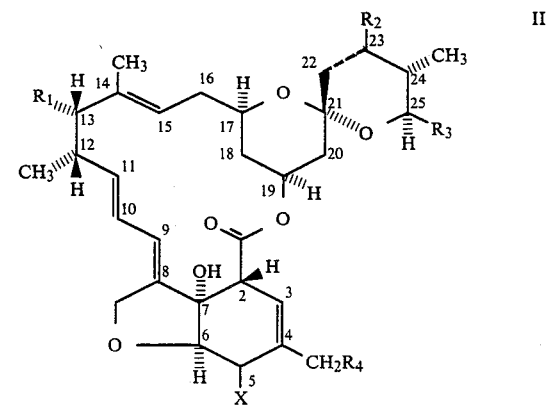

in which
  $R^1$, $R^2$, $R^3$ and $R^4$ have the abovementioned meaning and
  X stands for halogen,
are reduced.

3. New compounds of the formula II

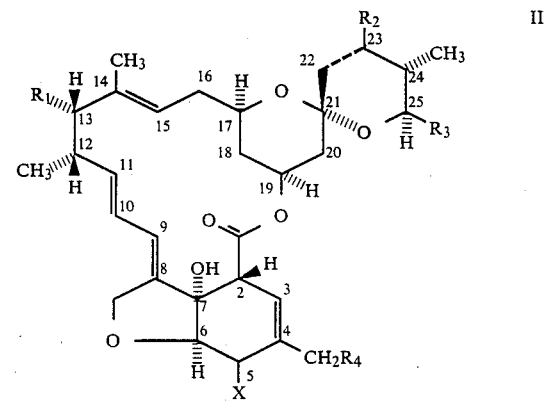

in which
  $R^1$ stands for hydrogen, OH, $C_{1-5}$-alkanoyloxy, α-L-oleandrosyloxy, α-L-oleandrosyl-α-L-oleandrosyloxy, 4'-$C_{1-5}$-alkanoyl-α-L-oleandrosyloxy or 4"-$C_{1-5}$-alkanoyl-α-L-oleandrosyl-α-L-oleandrosyloxy,
  $R^2$ stands for hydrogen, OH, $C_{1-5}$-alkanoyloxy, or $R^2$ stands for hydrogen when there is a double bond between C22 and C23,
  $R^3$ stands for straight-chain or branched alkyl or alkenyl,
  $R^4$ stands for hydrogen, OH, $C_{1-5}$-alkanoyloxy, heterocyclylcarbonyloxy, or the bond between the C atoms C22 and C23 is a single or a double bond and the double bond of the cyclohexene ring can be between the C atoms C3 and C4 or between the C atoms C4 and C5 and
X stands for halogen.

4. Process for the preparation of compounds of the formula II according to 2 (above), characterized in that compounds of the formula II in which X stands for the radical —OSO$_2$—R$^5$ wherein
R$^5$ stands for alkyl, halogenoalkyl, aryl or substituted aryl, are reacted with halides, or compounds of the formula II in which X stands for OH, are reacted with arylsulphonyl halides in the presence of dimethylaminopyridine.

It is known of the avermectins that the acaricidal action of the compounds is lowered by alteration of the substitution on C atom 5 (R. A. Dybar et al. 1984 British Crop Protection Conference Pests and Diseases 9B-3 pages 947–54). Surprisingly, it has been found that derivatives of avermectins which are unsubstituted on C atom 5 exhibit an outstanding action against ticks. They can therefore preferably be used as ecto- and endoparasiticides in animals.

Preferred compounds of the formula I are those in which

R$^1$ stands for hydrogen, OH, acetoxy or α-L-oleandrosyl-α-L-oleandrosyloxy,
R$^2$ stands for hydrogen, OH or acetoxy,
R$^3$ stands for C$_{1-4}$-alkyl, in particular methyl, ethyl, isopropyl, sec.-butyl, C$_{2-8}$alkenyl, in particular 2-buten-2-yl, 4-methyl-pent-2-en-2-yl or 4-methyl-hex-2-en-2-yl,
R$^4$ stands for hydrogen, there is a single bond between C22 and C23, there is a double bond between C3 and C4, and there is a single bond between C4 and C5.

Particularly preferred are those compounds of the formula I in which

R$^1$ stands for α-L-oleandrosyl-α-L-oleandrosyloxy,
R$^2$ stands for hydrogen,
R$^3$ stands for isopropyl or sec.-butyl,
R$^4$ stands for hydrogen, there is a single bond between C22 and C23, there is a double bond between C3 and C4, and there is a single bond between C4 and C5.

The compounds of the formula I are obtained by reducing compounds of the formula II. Suitable reductants are preferably organic tin hydrides such as, for example, tributyltin hydride, tricyclohexyltin hydride, triphenyltin hydride, in the presence of radical-forming catalysts such as, for example, peroxides or azobisisobutyronitrile.

The reaction is carried out with exclusion of moisture in organic solvents which are inert under the reaction conditions. These include aliphatic and aromatic hydrocarbons, hexane, cyclohexane, benzene, toluene, xylene, cyclic ethers such as tetrahydrofuran, dioxane, and furthermore dimethylformamide.

The reaction is carried out at temperatures between 20° and 100° C., preferably between 40° and 60° C.

The reaction is preferably carried out at atmospheric pressure. After the reaction has taken place, the batch is purified chromatographically.

Compounds of the formula II are new. Preferred compounds of the formula II are those in which the substituents R$^1$, R$^2$, R$^3$ and R$^4$ have the preferred meanings given in the case of the compounds of the formula I and X stands for chlorine or bromine.

Compounds of the formula II in which X stands for halogen are obtained by reacting compounds of the formula II in which X stands for the radical of the formula —O—SO$_2$—R$^5$ with halides. Some of these commpounds are known or can be prepared in analogy to known processes (CA 101; 23 232 v, CA 99; 194 690 n, CA 98; 89 075 x).

Compounds of the formula II in which X stands for OSO$_2$R$^5$ and R$^5$ stands for p-toloyl or C$_{1-6}$-alkyl are preferably employed as starting compounds.

Alkali metal halides such as KBr, KCl, quaternary ammonium halides and hydrogen halide complexes of optionally substituted pyridines are preferably employed as halides.

The reaction is carried out in diluents which are inert under the reaction conditions. These include optionally halogenated hydrocarbons such as light petroleum, benzine, cyclohexane, toluene, xylene, chloroform, dichloromethane, o-dichlorobenzene, ethers such as diethyl ether, tetrahydrofuran, dioxane, ketones such as acetone, esters such as ethyl acetate, DMSO and DMF.

The reaction is carried out between −40° C. and 80° C., preferably between 20° C. and 50° C.

About 1–5 moles, preferably 1–2 moles, of halide are employed per mole of compound of the formula II.

The reaction mixture is preferably chromatographically separated after completion of the reaction.

Compounds of the formula II in which X stands for Cl can also be prepared by reacting the known compounds of the formula II in which X stands for OH with arylsulphonyl halides, preferably p-toluenesulphonyl chloride or o-nitrobenzenesulphonyl chloride, in the presence of dimethylaminopyridine and in the presence of a diluent. Suitable diluents are the diluents described further above. The reaction is carried out between −10° and +50° C., preferably between 20° and 40° C. About 1–1.5 moles, preferably about 1.2 mole of aryl, preferably p-toluenesulphonyl chloride, are employed per mole of compound of the formula II.

The active compounds are suitable for combating animal pests such as arthropods, preferably insects and spiders, which are encountered in animal production and animal breeding of domestic and productive animals and also zoo, laboratory, experimental and pet animals and have favourable toxicity to warm-blooded animals. They are thus active against all or some stages of development of the pests and also against resistant and normally sensitive species of the pests.

By combating the animal pests, it is intended to reduce diseases and their transmission, cases of death and reduction in productivity (for example in the production of meat, milk, wool, hides and eggs), so that more economic and simpler animal production is possible, or in certain areas is only possible, by using of the active compounds.

The pests include:

From the order of the Anoplura, for example, Haematopinus spp., Linognathus spp., Solenopotes spp., Pediculus spp. and Pthirus spp.; from the order of the Mallophaga, for example, Trimenopon spp., Menopon spp., Eomenacanthus spp., Menacanthus spp., Trichodectes spp., Felicola spp., Damalinea spp. and Bovicola spp; from the order of the Diptera, for example, Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp. and Hippobosca spp..

From the order of the Siphonaptera, for example, Ctenocephalides spp., Echidnophaga spp. and Ceratophyllus spp..

From the order of the Metastigmmata, for example, Hyalomma spp., Rhipicephalus spp., Boophilus spp., Amblyomma spp., Haemaphysalis spp., Dermacentor spp., Ixodes spp., Argas spp., Ornithodorus spp. and Otobius spp.; from the order of the Mesastigmata, for example, Dermanysus spp., Ornithonyssus spp. and Pneumonyssus spp..

From the order of the Prostigmata, for example, Cheyletiella spp., Psorergates spp., Myobia spp., Demodex spp. and Neotrombicula spp.; from the order of the Astigmata, for example, Acarus spp., Myocoptes spp., Psoroptes spp., Chorioptes spp., Otodectes spp., Sarcoptes spp., Notoedres spp., Knemidocoptes spp., Neoknemidocoptes spp. Lytodites spp. and Laminosioptes spp..

The domestic and productive animals include mammals such as, for example, cattle, horses, sheep, pigs, goats, dogs, cats, camels, waterbuffalo, donkeys, rabbits, fallow deer and reindeer, pelt animals such as, for example, mink, chinchilla and racoons, and poultry such as, for example, chickens, geese, turkeys, pheasants and ducks.

The laboratory and experimental animals include, for example, mice, rats, guineapigs, golden hamsters, dogs and cats.

The pet animals include, for example, dogs and cats.

Administration can take place either prophylactically or therapeutically.

Administration of the active compounds takes place enterally, parenterally, dermally or nasally directly or in the form of suitable preparations, by treatment of the environment or with the aid of moulded articles containing the active compound such as, for example, strips, sheets, bands, neckbands, eartags, limb bands and marking devices.

Enteral administrationn of the active compounds occurs, for example, orally in the form of powders, tablets, capsules, pastes, boli, drinks, granules, orally applicable solutions, suspensions or emulsions, or medicated feed or drinking water. Dermal administration occurs, for example, in the form of dipping, spraying or pouring on and spotting on and powdering. Parenteral administration occurs, for example, in the form of injections (for example intramuscular, subcutaneous or intravenous) or by implants.

Compositions for dermal administration may be particularly emphasized. These include solutions, suspension and emulsion concentrates and also microemulsions which are diluted using water before administration, formulations for pouring on, powders and dusts, aerosols and moulded articles containing the active compound, and also dust-bags and back rubbers.

These compositions are produced in a known manner, for example, by mixing the active compound with extenders, thus, for example, liquid solvents, if appropriate using surface-active agents, such as emulsifiers and/or dispersants. In the case of the use of water as extender, organic solvents can also be used, for example, as auxiliary solvents.

In addition to water, the liquid diluents include alcohols such as methanol, ethanol, isopropanol, n-butanol, amyl alcohol and octanol; glycols such as propylene glycol, 1,3-butylene glycol, ethyl glycol and dipropylene glycol monomethyl ether; glycerol; aromatic alcohols such as benzyl alcohol; carboxylic acid esters such as, for example, ethyl acetate, benzylbenzoate, butyl acetate, propylene carbonate and ethyl lactate; aliphatic hydrocarbons such as paraffins, cyclohexane, methylene chloride and ethylene chloride; aromatic hydrocarbons such as xylene, toluene, alkylnaphthalenes and chlorobenzenes; ketones such as, for example, acetone and methyl ethyl ketone, methyl isobutyl ketone and cyclohexanone; natural and synthetic mono and triglycerides containing natural fatty acids such as cottonseed oil, groundnut oil, corn germ oil, olive oil, castor oil or sesame oil; and furthermore dimethyl sulphoxide, dimethylacetamide, dimethylformamide, N-methylpyrrolidone, dioxane and 2,2-dimethyl-4-oxymethyl-1,3-dioxolane.

The surface-active substances include: emulsifiers and wetting agents such as anionic surfactants, for example alkyl sulphonates, alkyl sulphates, aryl sulphonates, Na lauryl sulphates, fatty alcohol ether sulphates, mono/dialkyl polyglycol ether orthophosphate monoethanolaminne salt and calcium alkylaryl sulphonate; cationic surfactants, for example cetyltrimethylammonium chloride; ampholytic surfactants, for example di-Na-N-lauryl beta-iminodipropionate or lecithin; nonionic surfactants, for example polyoxyethylated castor oil, polyoxyethylated sorbitan monooleate, polyoxyethylated sorbitan monostearate, glycerol monostearate, polyoxyethylene stearate, alkylphenol polyglycol ether, polyoxyethylated sorbitan monopalmitate, polyoxyethylene lauryl ether, polyoxyethylene oleyl ether, polyoxyethylene mannitan monolaurate, alkyl polyglycol ether, oleyl polyglycol ether, dodecyl polyglycol ether, ethoxylated nonylphenol and isooctylphenol polyethoxyethanol.

The compositions can additionally contain: adhesion promoters, for example carboxymethylcellulose, methylcellulose and other cellulose and starch derivatives, polyacrylates, alginates, gelatines, gum arabic, polyvinylpyrrolidone, polyvinyl alcohol, copolymers of methyl vinyl ether and maleic anhydride, polyethylene glycols, paraffins, oils, waxes, hydrogenated castor oil, lecithins and synthetic phospholipids.

The compositions can contain colorants such as inorganic pigments, for example iron oxide, titanium oxide, Prussian blue and organic dyestuffs, such as alizarin dyestuffs, azo dyestuffs and metal phthalocyanine dyestuffs.

The compositions can contain spreading agents, for example silicon oils of differing viscosity, fatty acid esters such as ethyl stearate, di-n-butyl adipate, hexyl laurate, dipropylene glycol pelargonate, esters of a branched fatty acid of medium chain length with saturated $C_{16}$–$C_{18}$ fatty alcohols, isopropyl myristate, isopropyl palmitate, caprylates/caprates of saturated fatty alcohols of chain length $C_{12}$–$C_{18}$, isopropyl stearate, oleyl oleate, decyl oleate, ethyl oleate, ethyl lactate, waxy fatty acid esters, dibutyl phthalate, di-isopropyl adipate, and lastly related ester mixtures inter alia; triglycerides such as caprylic/capric acid triglyceride, triglyceride mixtures with vegetable fatty acids of chain length $C_8$–$C_{12}$ or other. specifically selected natural fatty acids, partial glyceride mixtures of saturated or unsaturated and also hydroxyl group-containing fatty acids, monodiglycerides of $C_8/C_{10}$-fatty acids and others; and fatty alcohols such as isotridecyl alcohol, 2-octyldodecanol, cetyl stearyl alcohol and oleyl alcohol.

For the production of solid compositions, the active compound is mixed with suitable excipients if appropriate with the addition of auxiliaries and brought into the desired form.

Excipients which may be mentioned are all physiologically compatible solid inert substances. Those which are suitable are inorganic and organic substances. Inorganic substances are crushed and fractionated if necessary, for example synthetic and natural ground minerals such as kaolins, talc, chalk, quartz, diatomaceous earth, sodium chloride, carbonates such as calcium carbonate, hydrogen carbonates, aluminum oxides, silicic acids, aluminas, precipitated or colloidal silica and phosphates.

Organic substances are, for example, sugar, cellulose, food and feedstuffs such as powdered milk, animal meals, cereal meals and shreds, starches and sawdust.

Auxiliaries are preservatives, antioxidants and colorants, which have already been listed further above.

Further suitable auxiliaries are lubricants and glidants such as, for example, magnesium stearate, stearic acid, talc, bentonites, disintegration-promoting substances such as starch or cross-linked polyvinylpyrrolidone, binding agents such as, for example, starch, gelatine or linear polyvinylpyrrolidone and also dry binding agents such as microcrystalline cellulose.

The active compounds can also be encapsulated in the form of their abovementioned solid or liquid formulations.

The active compounds can also be administered in the form of an aerosol. In this case, the active compound is present finely divided in a suitable formulation under pressure.

It can also be advantageous to administer the active compounds in formulations which retard the release of the active compound. Those which may be mentioned are moulded articles containing the active compound such as, for example, sheets, bands, strips, neckbands, ear tags, tail marks, limb bands, halters and marking devices. Implants and boli containing the active compound may also be mentioned.

The administration of the active compounds can take place together with the feed and/or the drinking water.

The active compounds can be present in the formulations alone or in a mixture with other active compounds or synergists.

Directly administered formulations contain between $10^{-7}$ and 5 percent by weight, preferably between $10^{-4}$ and 1 percent by weight, of active compound.

Formulations which are only applied after further dilution contain 1–95 percent by weight, preferably 5–90 percent by weight of active compound.

EXAMPLE A

Test with *Boophilus microplus* resistant

Solvent:
35 parts by weight of ethylene glycol monomethyl ether
35 parts by weight of nonylphenol polyglycol ether.

To produce a suitable preparation of active compound, three parts by weight of active compound are mixed with seven parts by weight of the solvent mixture indicated above, and the concentrate thus obtained is diluted with water to the desired concentration.

10 adult *Boophilus microplus* res. are immersed for 1 minute in the active compound preparation to be tested. After transfer to plastic beakers and storage in a climatically controlled chamber, the degree of destruction is determined.

In this test, for example, the following compounds from the preparation examples show a superior action compared to the prior art: Example 1.

EXAMPLE B

Test with *Psoroptes ovis*

Solvent:
35 parts by weight of ethylene glycol monomethyl ether
35 parts by weight of nonylphenol polyglycol ether.

To produce a suitable preparation of active compound, three parts by weight of active compound are mixed with seven parts by weight of the solvent mixture indicated above, and the concentrate thus obtained is diluted with water to the desired concentration.

About 10–25 Psoroptes ovis are introduced into 1 ml of the active compound preparation to be tested, which has been pipetted into tablet nests of a deep-drawn pack. After 24 hours the degree of destruction is determined.

In this test, the following compounds of the preparation examples display a superior action compared to the prior art: Example 1

PREPARATION EXAMPLES

EXAMPLE 1

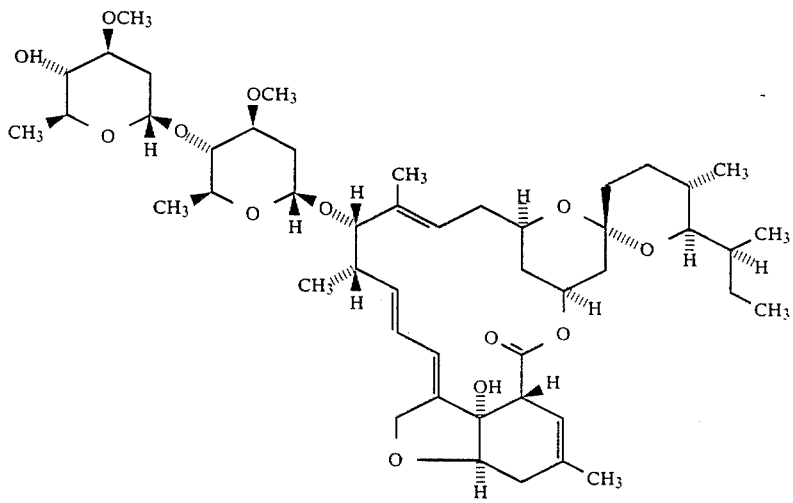

1.2 g of the compound of the formula IIa substituted with bromine in the 5-position are dissolved in 10 ml of absolute toluene, 2.0 ml of tributyltin hydride are added and 200 mg of azobisisobutyronitrile are added. The mixture is warmed to 50° C. After 2 hours, the mixture is added to a columnn of silica gel 60 (Merck 230–400 mesh) equilibrated using toluene, and the organotin compounds are eluted using toluene. The compound of the formula Ia is eluted using toluene/ethyl acetate 8:1.

EXAMPLE 2

Starting from 1.2 g of the compound according to formula II a substituted with chlorine in the 5-position, the compound of the formula I a is obtained analogously to Example 1.

Preparation of the starting compounds according to processes 6 and 4:

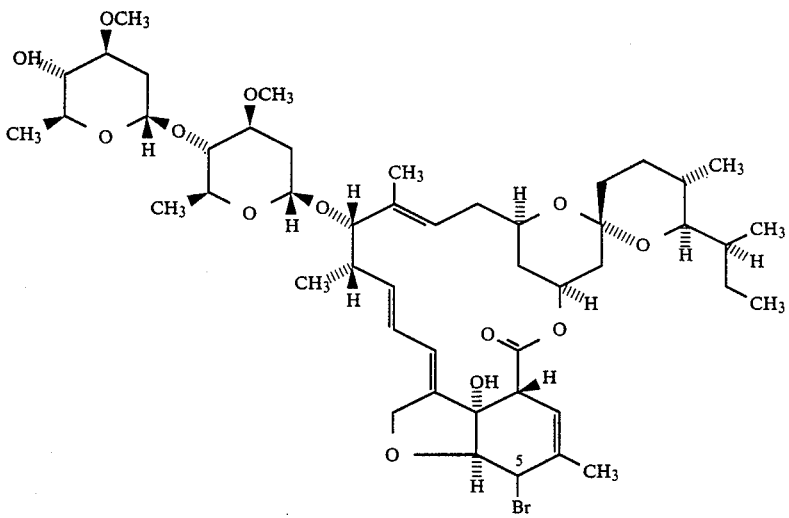

EXAMPLE a 7.0 g of the compound of the formula IIa substituted with OH in the 5-position are dissolved in 50 ml of dry ethanol-free chloroform, 6.5 ml of absolute pyridine are added and the solution is cooled to $-25°$ C. A solution of 1.0 ml of methanesulphonyl chloride in 5.0 ml of absolute chloroform is slowly added dropwise to this solution. The reaction is complete after about 2 hours. Excess methanesulphonyl chloride is decomposed by addition of 1.0 ml of methanol. The batch is washed using phosphate buffer and water, dried over magnesium sulphate and concentrated. The crude syrup is directly reacted further to the compound of the formula IIa.

The crude syrup obtained is dissolved in 50 ml of dry chloroform, and 10 g of tetrabutylammonium bromide are added. The reaction is complete after about 4 hours (thin layer chromatographic detection: first by spraying with a 0.1 percent ethanolic fluorescein solution, drying and spraying with acetic acid/perhydrol 1:1, and then heat treatment). For working up, the batch is concentrated, taken up in toluene and concentrated again. The residue is chromatographed in toluene/acetone 8:1. 5 g of the compound of the formula IIa substituted in the 5-position by bromine are obtained.

EXAMPLE b 3.0 g of the compound of the formula IIa substituted in the 5-position by OH are dissolved in 25 ml of absolute chloroform and 3.0 g of tosyl chloride and 3.0 g of dimethylaminopyridine are added with ice-cooling. As soon as the reaction to the 5-O-monotosylate is complete, excess tosyl chloride is decomposed using methanol. The batch is then left for a further 5 hours at room temperature. For working up, the batch is first washed using aqueous phosphate buffer and then using water. The organic phase is dried over magnesium sulphate and concentrated. For purification, the residue is chromatographed on silica gel in toluene/acetone 5:1. The compound of the formula II a substituted with chlorine in the 5-position is obtained.

It will be appreciated that the instant specification and claims are set forth by way of illustration and not limitation, and that various modifications and changes may be made without departing from the spirit and scope of the present invention.

What is claimed is:
1. An avermectin derivative of the formula

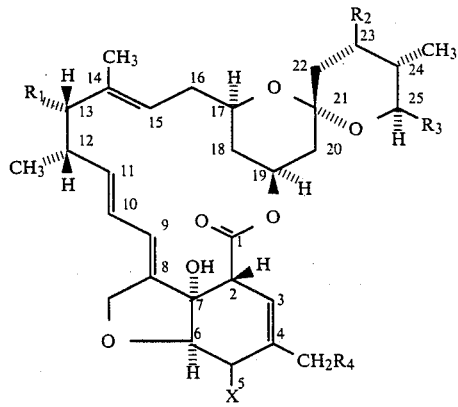

in which
R[1] stands for hydrogen, OH, $C_{1-5}$-alkanoyloxy, α-L-oleandrosyloxy, α-L-oleandrosyl-α-L-oleandrosyloxy, 4′-$C_{1-5}$-alkanoyl-α-L-oleandrosyloxy or 4″-$C_{1-5}$-alkanoyl-α-L-oleandrosyl-α-L-oleandrosyloxy, $R^2$ stands for hydrogen, OH, $C_{1-5}$-alkanoyloxy, or $R^2$ stands for hydrogen when there is a double bond between C22 and C23, $R^3$ stands for straight-chain or branched $C_{1-4}$-alkyl or $C_{2-8}$-alkenyl, $R^4$ stands for hydrogen, OH, $C_{1-5}$-alkanoyloxy, or the bond between the C atoms C22 and C23 is a single or a double bond and the double bond of the cyclohexene ring can be between the C atoms C3 and 4 or between the C atoms C4 and C5, and X stands for hydrogen or halogen.

2. A compound according to claim 1, in which X is hydrogen.

3. A compound according to claim 2 of the formula

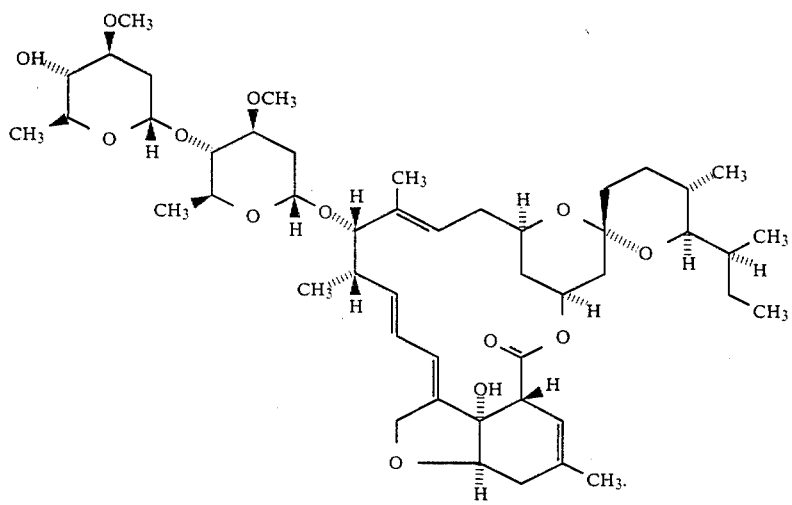

4. A compound according to claim 1, in which X is halogen.

5. A parasiticidal composition comprising a parasiticidally effective amount of a compound according to claim 2 and a diluent.

6. A method of combating parasites which comprises applying to such parasites or to an animal habitat for such parasite a parasiticidally effective amount of a compound according to claim 2.

7. The method according to claim 6, wherein such compound is of the formula

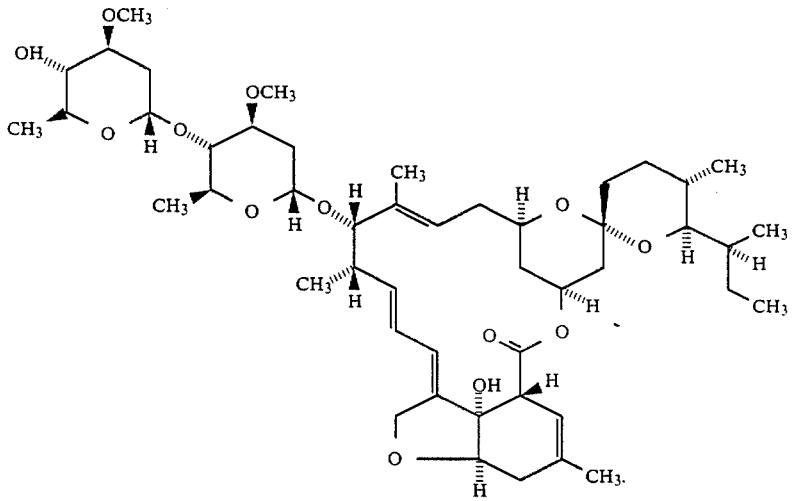

* * * * *